US00PP34435P3

(12) United States Plant Patent
Olesen

(10) Patent No.: US PP34,435 P3
(45) Date of Patent: Jul. 26, 2022

(54) MINIATURE ROSE PLANT NAMED 'POULPAR123'

(50) Latin Name: *Rosa hybrida*
Varietal Denomination: 'Poulpar123'

(71) Applicant: Mogens Nyegaard Olesen, Fredensborg (DK)

(72) Inventor: Mogens Nyegaard Olesen, Fredensborg (DK)

(73) Assignee: Poulsen Roser A/S, Fredensborg (DK)

( * ) Notice: Subject to any disclaimer, the term of this patent is extended or adjusted under 35 U.S.C. 154(b) by 0 days.

(21) Appl. No.: 17/300,617

(22) Filed: Sep. 7, 2021

(65) Prior Publication Data

US 2022/0095505 P1 Mar. 24, 2022

(51) Int. Cl.
*A01H 6/74* (2018.01)
*A01H 5/02* (2018.01)

(52) U.S. Cl.
USPC ..... Plt./116
CPC ..... *A01H 6/749* (2018.05)

(58) Field of Classification Search
USPC ..... Plt./116
See application file for complete search history.

(56) References Cited

PUBLICATIONS

Upov Pluto result 2022.*

* cited by examiner

*Primary Examiner* — Annette H Para

(57) ABSTRACT

A new garden rose plant of the Miniature class which has abundant, yellow flowers and attractive foliage. This new and distinct variety has shown to be uniform and stable in the resulting generations from asexual propagation.

2 Drawing Sheets

Botanical designation: *Rosa hybrida.*
Variety denomination: 'Poulpar123'.

This application claims priority to Plant Breeder's Rights Application Number 2020/2267, which was filed at the Community Plant Variety Rights Office in the European Union on Sep. 21, 2020, the contents of which are hereby incorporated by reference for all purposes.

SUMMARY OF THE INVENTION

The present invention constitutes a new and distinct variety of rose plant which originated from a controlled crossing between the female seed parent, an unnamed seedling, and the male pollen parent, also an unnamed seedling. Both of the parent varieties are non-patented.

The two parents were crossed during the summer of 2011 and the resulting seeds were planted in a controlled environment in Fredensborg, Denmark. The new variety, named 'Poulpar123', originated as a single seedling from the stated cross.

The new variety may be distinguished from its male pollen parent and female seed parent primarily by the following characteristics. The male pollen parent plant has white flowers while the new variety has yellow flowers. The female seed parent plant yellow orange flowers while the new variety has yellow flowers.

The objective of the hybridization of this rose variety was to create a new and distinct variety with unique qualities, such as:

1. Uniform and abundant yellow flowers;
2. Vigorous, but compact growth when propagated on its own roots;
3. Exceptional disease resistance.

This combination of qualities is not present in previously available commercial cultivars of this type, known to the inventor, and distinguish 'Poulpar123' from all other varieties of which we are aware.

As part of the rose development program, Mogens N. Olesen germinated the seeds from the aforementioned hybridization during winter of 2011 and conducted evaluations on the resulting seedlings in a controlled environment in Fredensborg, Denmark. 'Poulpar123' was selected in the spring of 2012 by the inventor as a single plant from the progeny of the aforementioned hybridization.

Asexual reproduction of 'Poulpar123' by rooted cuttings was first done by Mogens N. Olesen in the nursery in Fredensborg, Denmark in July, 2012. This initial and other subsequent asexual propagations conducted in controlled environments have demonstrated that the characteristics of 'Poulpar123' are true to type and are transmitted from one generation to the next.

DESCRIPTION OF THE DRAWING

The accompanying color illustrations show as true as is reasonably possible to obtain in color photographs of this type, the typical characteristics of the buds, flowers, leaves, and stems, of 'Poulpar123'.

Specifically illustrated in FIG. 1 of the drawings are open flowers at various stages of development, flower petals detached showing receptacle and reproductive flower parts, and sepals detached.

Figure 1:
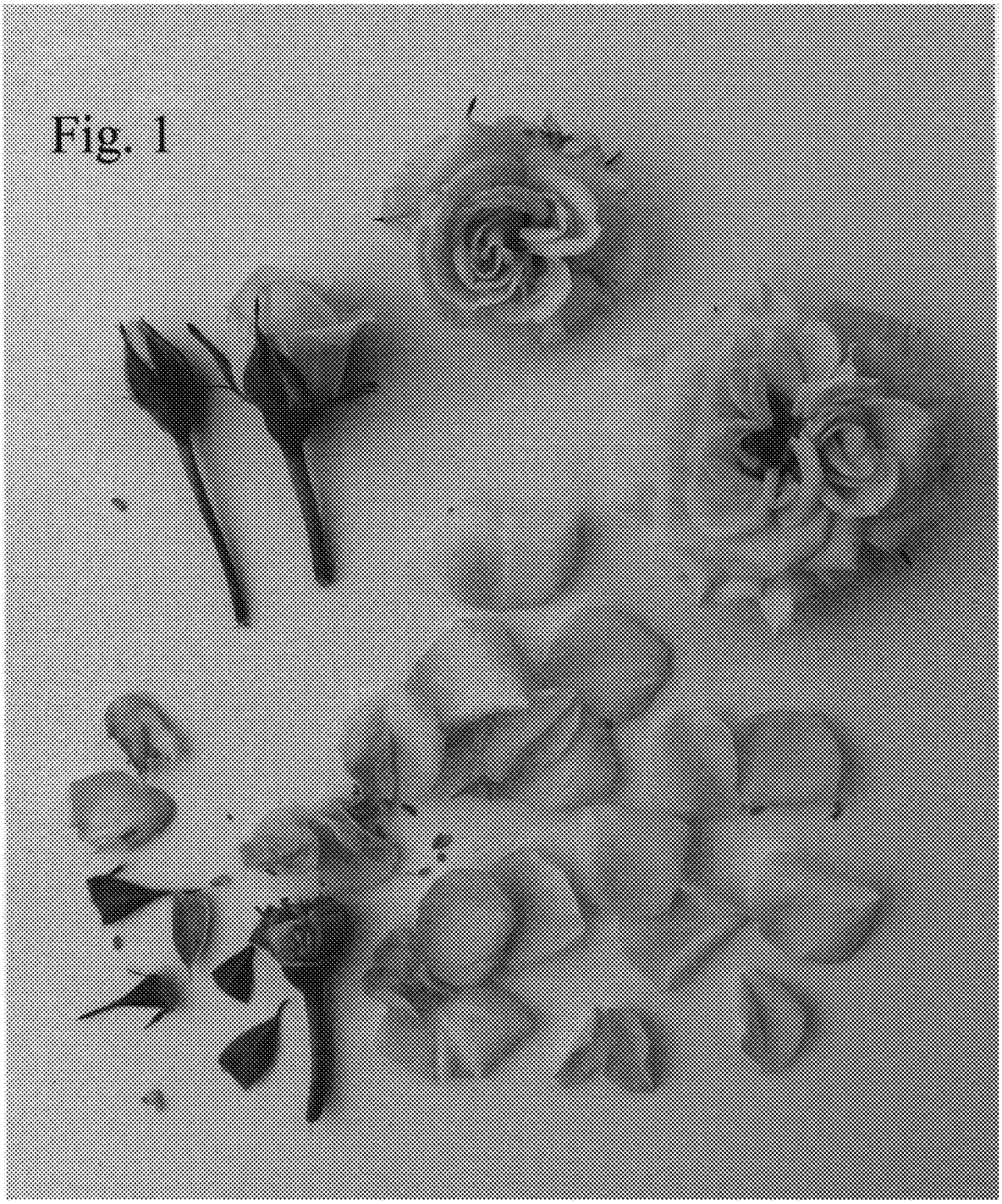
Figure 2:
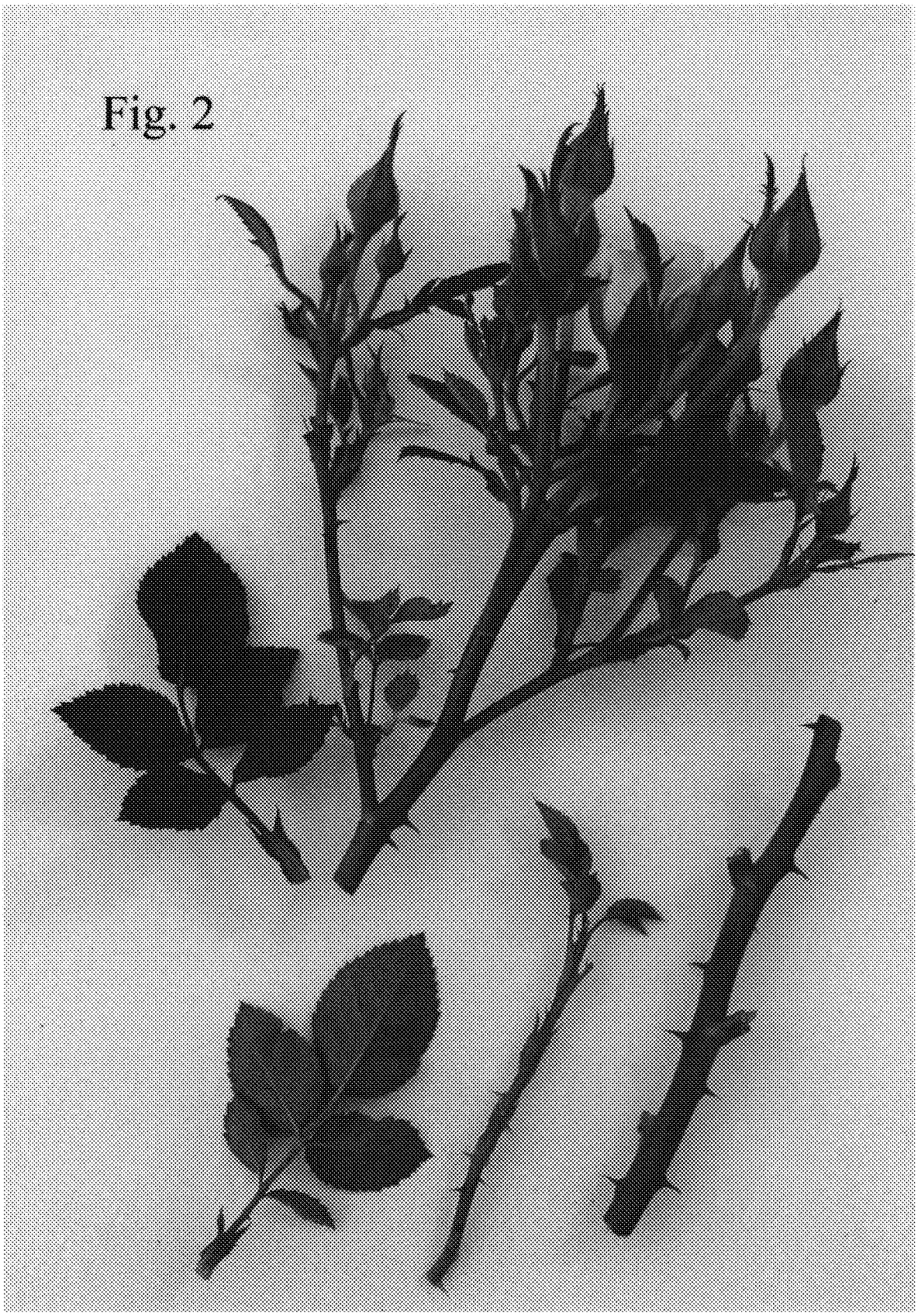

Specifically illustrated in FIG. 2 of the drawings is a cluster of flower buds on the branch, leaves, bare stem, and juvenile bare stem with juvenile leaves. Plants shown are 10 months of age.

DETAILED DESCRIPTION OF THE VARIETY

The following is a description of 'Poulpar123', as observed in its growth in an open air container nursery in Odense Denmark. Observed plants are 10 months of age, and were grown on their own roots in 24 cm pots. Color references are made using The Royal Horticultural Society (London, England) Colour Chart, 2001, except where common terms of color are used.

For a comparison, several physical characteristics of the rose variety 'Poulpar112', U.S. Plant patent application Ser. No. 16/602,258 are compared to 'Poulpar123' in Chart 1.

CHART 1

| | 'Poulpar123' | 'Poulpar112' |
|---|---|---|
| Petal Count | 56 | 35 |
| Flower Diameter | 65 mm | 60 |
| General Tonality of Flower Color | Open flowers are Yellow-Orange Group 19B with hints of Orange Group 25B | Yellow Group 12A |

Flower and flower bud:

*Blooming habit.*—Continuous.

*Flower bud.*—Size: Upon opening, 23 mm in length from base of receptacle to end of bud. Bud diameter is 15 mm. Bud form: Ovoid. Bud color: As sepals divide petals are Yellow-Orange Group 19A. Sepal inner surface: Color: Yellow-Green Group 146D. Surface: Lightly pubescent. Sepal outer surface: Color: Yellow-Green Group 144A with strong intonations of Greyed-Purple Group 183C. Texture: Smooth. Sepal shape: Apex: Cirrhose. Base: Flat at union with receptacle. Sepal margin: Margins have weak foliaceous appendages on three of the five sepals. Sepal size: 22 mm long, 10 mm wide. Receptacle: Texture: Smooth. Size: 5 mm in height, 11 mm wide. Color: Yellow-Green Group 144A with intonations of Greyed-Orange Group 175C. Shape: Campanulate. Pedicel: Surface: Smooth. Length: 25 mm. Diameter: 3 mm on average. Color: Yellow-Green Group 144A with intonations of Greyed-Red Group 180A. Strength: Strong. Peduncle: Length: About 2 to 6 cm. Diameter: 3 mm. Color: Yellow-Green Group 144A. Texture: Smooth.

*Flower bud development.*—Flower buds are borne in clusters of about 15 flower buds per stem. Development as a panicle.

*Flower bloom.*—Fragrance: Strong perfume. Duration: The blooms have a duration on the plant of approximately 10 days. Petals fall cleanly away from plant after flowers have fully matured. Size: Flower diameter is 56 mm when open. Flower depth is 24 mm. Flower shape: Tea. Shape of flower, side view: The upper portion is flat convex. The lower portion is flat.

*Petalage.*—Under normal conditions, flowers have about 65 petals.

*General tonality of flower.*—Open flowers are Yellow-Orange Group 19B with hints of Orange Group 25B.

*Petal color.*—Upon opening, outer petals: Upper surface: At the basal zone Yellow Group 12A which extends into the middle zone in shades. Yellow-Orange Group 18C at marginal zone. Lower surface: Yellow Group 11 D at apex. At middle zone Yellow-Orange Group 19A. Basal zone is Yellow Group 12A. Upon opening, inner petals: Upper surface: Basal zone is Yellow Group 9A. At the marginal zone Yellow-Orange Group 23D. Middle zone is Yellow-Orange Group 19A. Lower surface: Orange Group 25B mainly, with shades of Yellow-Orange Group 19B at margins. Yellow 9A at basal zone.

*Petals.*—Petal reflex: Somewhat reflexed. Margin: Entire and uniform. Light undulations. Shape: Round. Apex shape: Rounded. Base shape: Obtuse. Size: 30 mm (l)×31 mm (w). Texture: Smooth. Thickness: Average.

*Petaloids.*—Size: 10 mm (l) by 8 mm (w). Quantity: About 15. Shape: Elliptical with an acute base and rounded apices. Color: Orange Group 25A upper and lower surface, with petaloid spot Yellow Group 14A.

*Reproductive flower parts.*—Pollen: None observed. Anthers: Size: 2 mm in length. Color: Yellow-Orange Group 14A. Quantity: 32 on average. Filaments: Color: Yellow Group 12A. Length: 3 mm. Pistils: Length: 7 mm. Quantity: 24 on average. Stigmas: Color: Greyed-Yellow Group 161B. Styles: Color: Red Group 46C. Location of stigmas: Superior in location relative to the length of the filaments and the height of the anthers. Hips: None Observed.

Plant:

*Plant growth.*—Upright, compact. Plants are 38 cm in height, and 40 cm wide.

*Stems.*—Color of juvenile growth: Yellow-Green Group 144B with intonations of Greyed-Orange Group 175C. Color of mature growth: Yellow-Green Group 144A. Length: Canes are about 10 cm from the base of the plant to the flowering portion. Diameter: About 5 mm. Internodes: On mature canes about 22 mm between nodes. Surface texture: Young wood: Smooth. Older wood: Smooth.

*Long prickles.*—Incidence: 10 prickles per 10 cm of stem. Size: Average length of prickles on mature stems is 5 mm. Shape: Upper portion is linear. Lower portion is concave. Color: Juvenile prickles: Greyed-Red Group 181A. Mature prickles: Greyed-Red Group 181A.

*Plant foliage.*—Compound leaf: 105 mm (l)×80 (w). Quantity: 3 leaves per 10 cm of stem on average. Leaf bearing angle to the stem: 45 degrees. Color of juvenile foliage: Upper side: Yellow-Green Group 144A with intonations of Greyed-Purple Group 183B at margins. Lower side: Yellow-Green Group 144A shaded with Greyed-Purple Group 183B. Color of mature foliage: Upper side: Yellow-Green Group 146A. Lower side: Yellow-Green Group 146B.

*Plant leaves and leaflets.*—Stipules: Size: 20 mm long, 4 mm wide. Quantity: 2 per compound leaf. Shape: Linear, slightly broad based with outward extending apices. Margins: Lacerate. Color: Petiole: Length: 22 mm. Diameter: 2 mm. Upper surface color: Yellow-Green Group 144A with anthocyanic intonations of Greyed-Purple Group 183A. Lower surface color: Yellow-Green Group 144A. Rachis: Length: 42 mm. Upper surface color: Yellow-Green Group 144A with anthocyanic intonations of Greyed-Purple Group 183A. Lower surface color: Yellow-Green Group 144A. Leaflet: Quantity: Normally 5 leaflets. Margins: Serrated. Size: Terminal leaflets are about 46 mm long, 29 mm wide. Shape: Generally elliptical. Base: Rounded. Apex: Acute. Texture: Smooth.

Thickness: Average. Arrangement: Odd pinnate. Venation: Reticulate. Glossiness: Very glossy.

*Disease resistance.*—Above average resistance to powdery mildew *Sphaerotheca pannosa* var. *rosae*, downy mildew *Peronospora sparsa*, rust *Phragmidium* spp., black spot *Diplocarpon rosae*, and *Botrytis cinerea* under normal growing conditions.

*Cold hardiness.*—The variety is tolerant to USDA Cold Hardiness Zone 6.

*Heat tolerance.*—The variety has been found to be suitable for climate conditions found in the American Horticulture Society heat zone 7.

I claim:

1. A new and distinct variety of rose plant of the Miniature rose class named 'Poulpar123', substantially as illustrated and described herein, due to its abundant yellow flowers, disease resistance, and extended period of bloom.

* * * * *